US011464947B1

(12) United States Patent
Lim

(10) Patent No.: US 11,464,947 B1
(45) Date of Patent: Oct. 11, 2022

(54) AORTIC PERFUSION CATHETER

(71) Applicant: Kok Hoo Lim, Beavercreek, OH (US)

(72) Inventor: Kok Hoo Lim, Beavercreek, OH (US)

(*) Notice: Subject to any disclaimer, the term of this patent is extended or adjusted under 35 U.S.C. 154(b) by 0 days.

(21) Appl. No.: 17/565,752

(22) Filed: Dec. 30, 2021

(51) Int. Cl.
*A61M 25/10* (2013.01)
*A61M 1/36* (2006.01)
*A61M 25/00* (2006.01)

(52) U.S. Cl.
CPC ...... *A61M 25/1002* (2013.01); *A61M 1/3653* (2013.01); *A61M 1/3659* (2014.02); *A61M 25/1025* (2013.01); *A61M 25/10186* (2013.11); *A61M 2025/0042* (2013.01); *A61M 2202/0472* (2013.01); *A61M 2210/127* (2013.01)

(58) Field of Classification Search
CPC .......... A61F 2/95; A61F 2002/9505; A61F 2002/9511; A61F 2/9517; A61F 2/9522; A61F 2/9524; A61F 2/9525; A61F 2/9526; A61F 2002/9528; A61F 2002/9534; A61F 2/954; A61F 2/958; A61F 2002/9583; A61F 2002/9586; A61M 1/3659; A61M 1/3666; A61M 2025/1052; A61M 2210/127; A61M 25/007; A61M 25/10; A61M 1/3653; A61M 2025/0031; A61M 2025/0037; A61M 2202/0472; A61M 2210/125; A61M 25/0067; A61M 25/04; A61M 60/833; A61B 17/12109; A61B 17/12136; A61B 2017/00243; A61B 17/3421; A61B 2017/3419; A61B 2017/3425
See application file for complete search history.

(56) References Cited

U.S. PATENT DOCUMENTS 4,680,029 A * 7/1987 Ranford ............ A61M 25/0069
604/523
4,863,441 A * 9/1989 Lindsay ............ A61M 25/0054
604/523

(Continued)

OTHER PUBLICATIONS

Danielle O'Hara, BS, Allison McLarty, MD, Erick Sun, BA, Shinobu Itagaki, MS, MD, Henry Tannous, MD, Danny Chu, MD, Natalia Egorova, PhD, Joanna Chikwe, MD, Type-A Aortic Dissection and Cerebral Perfusion: The Society of Thoracic Surgeons Database Analysis, Original Article Adult Cardiac, vol. 110, Issue 5, p. 1461-1467, Nov. 1, 2020.

*Primary Examiner* — Adam Marcetich

(57) ABSTRACT

An aortic perfusion catheter is an apparatus that is used during surgery for acute ascending aortic dissection to reduce postoperative injuries from profound hypothermia, ischemia, and reperfusion. The apparatus may include at least one main cannula, an inflation cannula, a drainage cannula, and a balloon tamponade. The at least one main cannula helps maintain blood perfusion to the body during the procedure to reduce postoperative injuries. The inflation cannula enables the selective inflation and deflation of the balloon tamponade to facilitate the insertion and removal of the balloon tamponade along with the at least one main cannula within the descending thoracic aorta. The balloon tamponade prevents blood flow into the operative area to maintain the operative area clear during the procedure. The drainage cannula enables the drainage of blood that may escape the balloon tamponade as well as other bodily fluids.

11 Claims, 13 Drawing Sheets

(56) References Cited

U.S. PATENT DOCUMENTS

| | | | |
|---|---|---|---|
| 5,324,260 A * | 6/1994 | O'Neill | A61M 25/10182 604/103.08 |
| 5,334,142 A | 8/1994 | Paradis | |
| 5,697,905 A | 12/1997 | d'Ambrosio | |
| 5,820,593 A | 10/1998 | Safar | |
| 6,086,557 A * | 7/2000 | Morejohn | A61M 25/0041 604/509 |
| 6,117,105 A | 9/2000 | Bresnaham | |
| 6,547,760 B1 | 4/2003 | Samson | |
| 2001/0041858 A1 * | 11/2001 | Ray | A61B 17/3417 604/93.01 |
| 2001/0041864 A1 * | 11/2001 | Sweezer | A61M 25/1011 604/509 |
| 2002/0013569 A1 * | 1/2002 | Sterman | A61F 2/2427 604/509 |
| 2004/0162519 A1 * | 8/2004 | Helkowski | A61M 1/3659 604/103.09 |
| 2006/0142702 A1 * | 6/2006 | Sievers | A61M 25/007 604/264 |
| 2006/0155366 A1 * | 7/2006 | LaDuca | A61F 2/954 606/108 |
| 2006/0247575 A1 * | 11/2006 | Cartledge | A61M 1/3659 604/102.01 |
| 2007/0044807 A1 * | 3/2007 | Madsen | A61M 16/0479 128/207.15 |
| 2009/0112049 A1 * | 4/2009 | Ahmed | A61M 60/268 600/16 |
| 2014/0207060 A1 * | 7/2014 | Hochareon | A61M 1/3607 604/96.01 |
| 2016/0022409 A1 * | 1/2016 | Aharon | A61B 17/12136 623/1.24 |
| 2016/0135971 A1 * | 5/2016 | Tal | A61F 2/958 623/1.11 |
| 2018/0280664 A1 * | 10/2018 | Michler | A61M 25/10 |

* cited by examiner

AORTIC PERFUSION CATHETER

FIELD OF THE INVENTION

The present invention relates generally to medical equipment. More specifically, the present invention provides an aortic perfusion catheter that reduces postoperative injuries from profound hypothermia, ischemia, and reperfusion after open heart surgery on patients with acute ascending aortic dissection.

BACKGROUND OF THE INVENTION

Acute ascending aortic dissection is a serious heart condition that warrants emergency open heart surgery. In general, a patient with the established diagnosis of acute ascending aortic dissection is brought into the operating room and connected to the cardiopulmonary bypass circuit where cooling and warming of the patient's blood can be carried out. Surgical repair of the ascending aortic dissection can then be performed. There are many risks with emergency open heart surgery, such as ischemia. However, there are ways to try to mitigate these risks using different equipment and techniques. For example, profound hypothermia has been shown to protect the brain and visceral organs from ischemia for a certain period, 20 to 30 minutes at body temperature of 20 degrees Centigrade (C).

In patients with acute ascending aortic dissection, there are three established techniques to protect the brain during the hypothermic circulatory arrest:

1. Profound hypothermia, 20 degrees C., and circulatory arrest,
2. Profound hypothermia, circulatory arrest, and antegrade perfusion via axillary artery cannulation and clamping of the innominate artery, and,
3. Profound hypothermia, circulatory arrest, and retrograde perfusion through the superior vena cava.

At this stage of the surgery, the heart is arrested and protected by cold blood cardioplegia, hypothermia, and venting of the left ventricle through left ventricular (LV) vent is performed to keep the heart decompressed. The brain receives antegrade or retrograde perfusion, if these techniques are utilized, or just with profound hypothermia. Further, the head of the patient if covered with ice packs.

Perfusion of the rest of the body is suspended during the circulatory arrest. The visceral organs are being protected by profound hypothermia, slowing down the metabolic rate of the cells. However, when the perfusion to the body is restored and the body is rewarmed, the tissues of the body will sustain injuries from ischemia and reperfusion. The severity of ischemia and reperfusion injuries depend on the duration of the circulatory arrest, the temperature of the body, and the functional status of the end organs. Some of the postoperative complications following the surgery for acute ascending aortic dissection may be the sequela of the ischemia and reperfusion injuries during the circulatory arrest and profound hypothermia. As a result, the mortality of surgery for acute ascending aortic dissection remains high, about 20 percent. Therefore, there is a need for better medical tools and techniques that lower the possible postoperative injuries associated with surgery for acute ascending aortic dissection as well as to lower the mortality rate associated with the procedure.

SUMMARY OF THE INVENTION

The present invention provides an aortic perfusion catheter that is inserted into the lumen of the descending thoracic aorta to maintain perfusion to the rest of the body during repair of the artic arch or the distal ascending aorta. Similar to traditional catheters, the aortic perfusion catheter includes a balloon tamponade that can be selectively inflated to prevent egress of blood into the operative field. The main cannula of the aortic perfusion catheter is connected to an existing cardiopulmonary bypass circuit through a Y-connector. The other end of the aortic perfusion catheter is passed through the lumen of the aortic graft for repair, and into the lumen of the descending thoracic aorta. Thus, the blood flow to the rest of the body is restored. Another cannula is applied that flows into the axillary artery and to the brain to about 1 liter per minute. At the same time, the origin of the innominate artery and the left common carotid artery are clamped. When the distal aortic anastomosis is completed, the aortic perfusion catheter is removed, and a clamp is applied to the Y-connector.

With this approach and the use of the present invention, patients with acute ascending aortic dissection may need only moderate hypothermia during the surgery. Avoidance of profound hypothermia, ischemia, and reperfusion injuries will hopefully help reduce incidence of postoperative coagulopathy and bleeding complications as well as end-organ dysfunction for the kidney, liver, and other end organs and massive fluid shifts. The present invention can also be used for surgery of the aneurysm of the ascending aorta and the aorta arch. Additional features and benefits of the present invention are further discussed in the sections below.

DETAIL DESCRIPTIONS OF THE INVENTION

Figure 1:
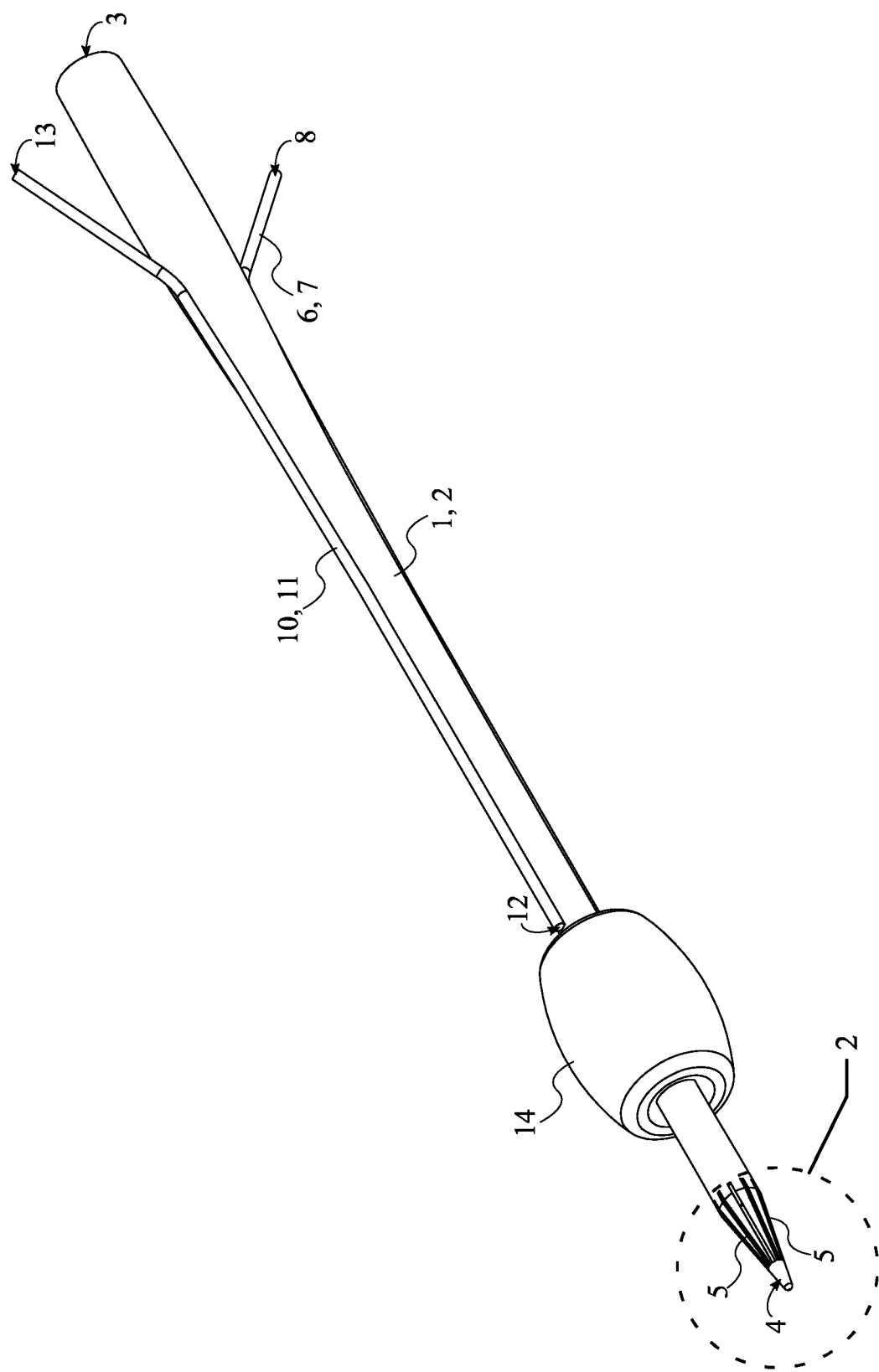
FIG. 1 is a top front perspective view showing the present invention.

All illustrations of the drawings are for the purpose of describing selected versions of the present invention and are not intended to limit the scope of the present invention.

The present invention is an aortic perfusion catheter that is used during surgery for acute ascending aortic dissection to reduce postoperative injuries from profound hypothermia, ischemia, and reperfusion. As can be seen in FIG. 1 through 4, the present invention may comprise at least one main cannula 1, an inflation cannula 6, a drainage cannula 10, and a balloon tamponade 14. The at least one main cannula 1 serves to maintain blood perfusion to the body during the procedure. The inflation cannula 6 enables the selective inflation and deflation of the balloon tamponade 14 to facilitate the insertion and removal of the balloon tamponade 14 along with the at least one main cannula 1 within the descending thoracic aorta. The drainage cannula 10 enables the drainage of blood that may escape the balloon tamponade 14 as well as other bodily fluids. The balloon tamponade 14 prevents blood flow into the operative area to maintain the operative area clear during the procedure.

The general configuration of the present invention enables medical staff to maintain blood perfusion to the body of the patient during open heart surgery to mitigate postoperative injuries. As can be seen in FIG. 1 through 7, the at least one main cannula 1 is an elongated structure designed to maintain a desired flow of blood back into the body. To do so, the at least one main cannula 1 comprises a main cannula body 2, a main cannula inlet 3, and a main cannula outlet 4. The main cannula inlet 3 and the main cannula outlet 4 correspond to the end openings of the main cannula body 2. Similarly, the inflation cannula 6 comprising an inflation cannula body 7, an inflation cannula inlet 8, and an inflation cannula outlet 9. The inflation cannula inlet 8 and the inflation cannula outlet 9 correspond to the end openings of the inflation cannula body 7. Further, the drainage cannula 10 comprises a drainage cannula body 11, a drainage cannula inlet 12, and a drainage cannula outlet 13. Like the inflation cannula 6, the drainage cannula inlet 12 and the drainage cannula outlet 13 correspond to the end openings of the drainage cannula body 11. To form a single structure, the inflation cannula body 7 and the drainage cannula body 11 are laterally connected to the main cannula body 2. This forms a three-cannula structure that can be inserted into the desired lumen.

In addition, the inflation cannula body 7 and the drainage cannula body 11 are positioned offset to each other to maintain both cannula bodies separate from each other. As can be seen in FIG. 1 through 7, the balloon tamponade 14 is laterally connected around the main cannula body 2, adjacent to the main cannula outlet 4. Thus, the balloon tamponade 14 moves along with the main cannula body 2 as the main cannula outlet 4 is inserted into the desired lumen. Further, the inflation cannula inlet 8 is positioned adjacent to the main cannula inlet 3 so that the inflation cannula inlet 8 is accessible to be connected to an inflation valve 20. This enables the user to selectively inflate or deflate the balloon tamponade 14. In addition, the inflation cannula outlet 9 hermetically traverses into the balloon tamponade 14 so that no fluid escapes the balloon tamponade 14. The drainage cannula inlet 12 is also positioned external to the balloon tamponade 14 so that the blood flow through the main cannula body 2 is not obstructed by the inflation of the balloon tamponade 14. Further, the drainage cannula outlet 13 is positioned adjacent to the main cannula inlet 3, so any undesired bodily fluid is drained out of the patient's body.

Figure 2:
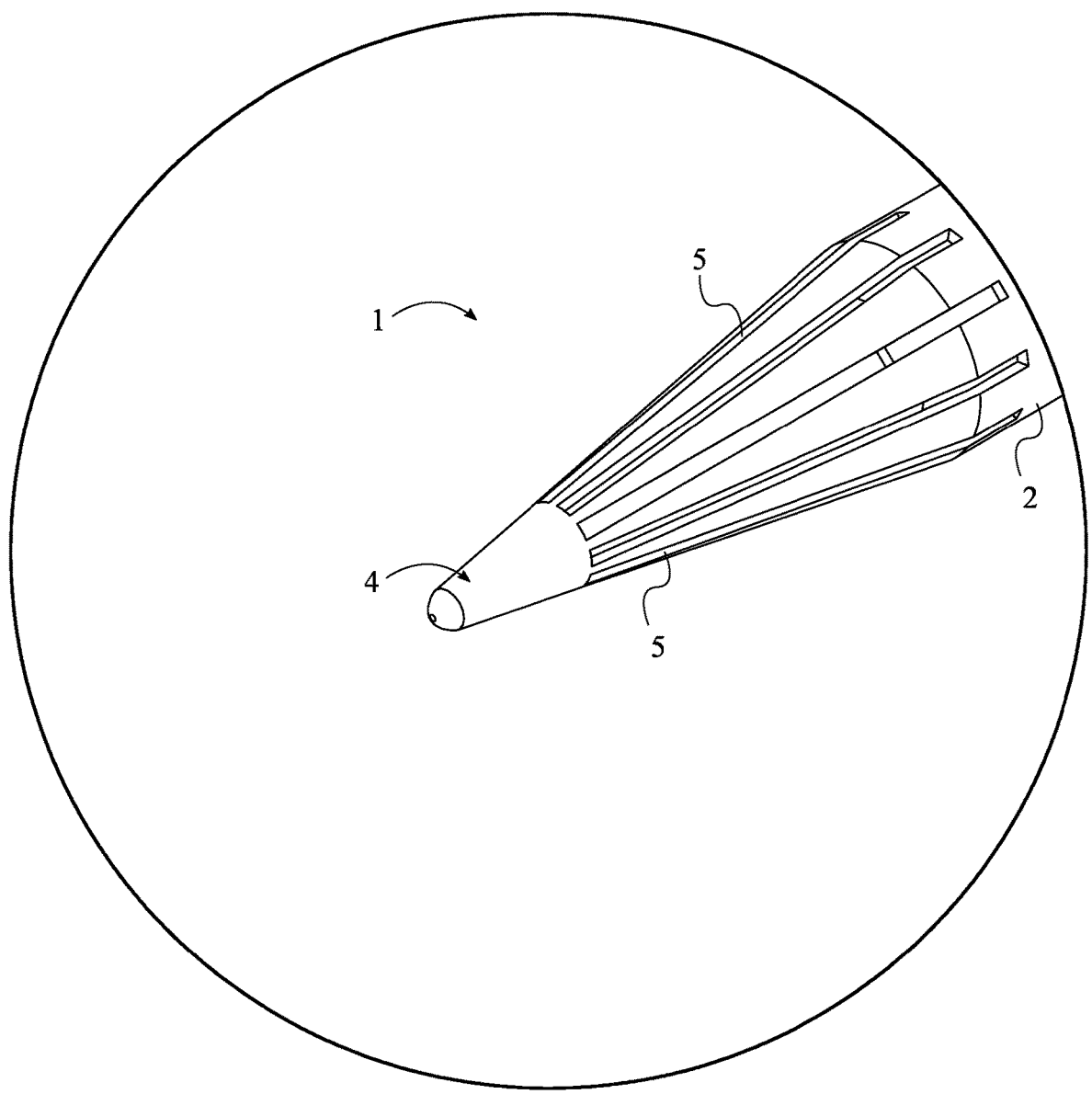
FIG. 2 is a magnified view of the main cannula outlet and the plurality of orifices shown in FIG. 1.
Figure 3:
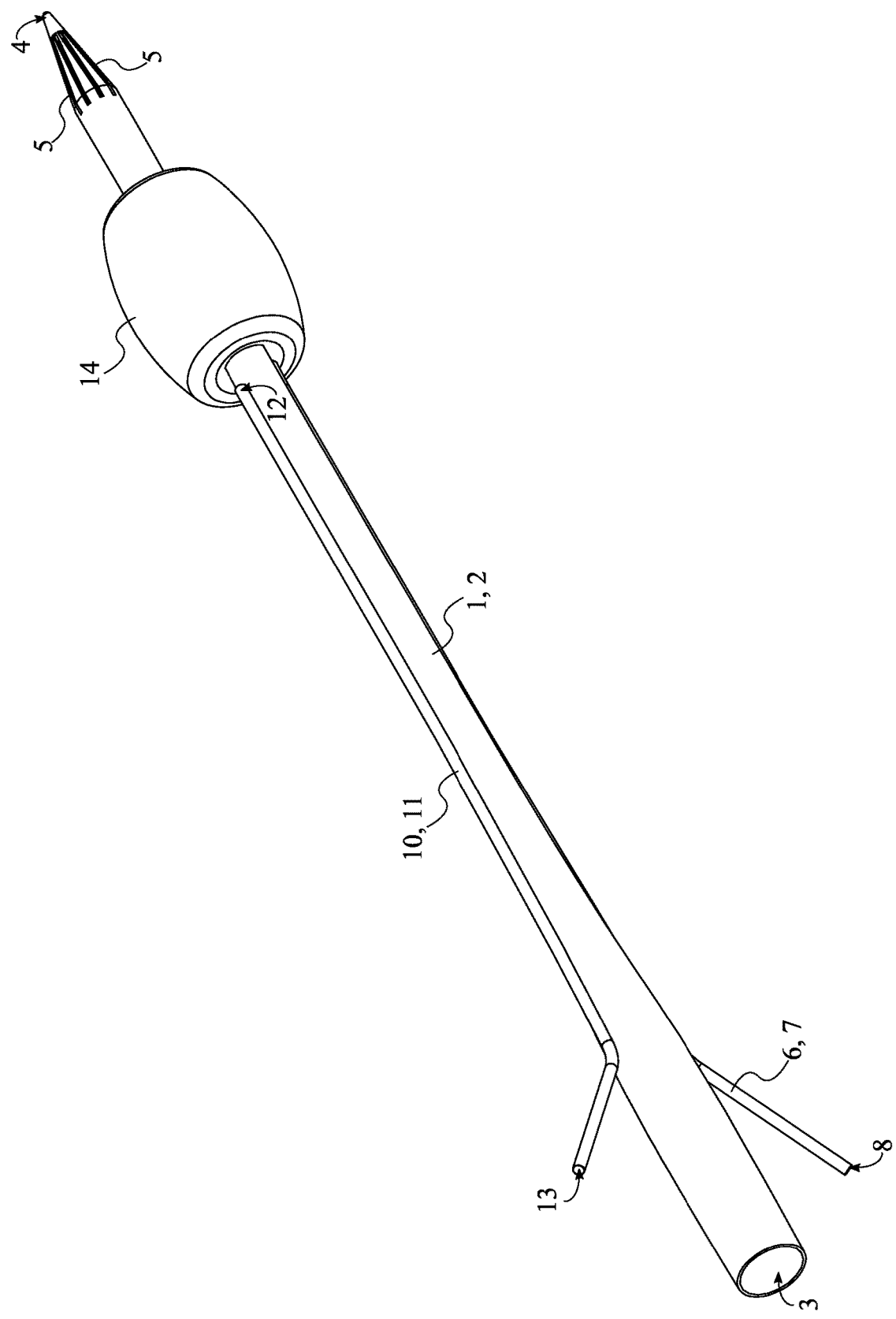
FIG. 3 is a top rear perspective view showing the present invention.
Figure 4:
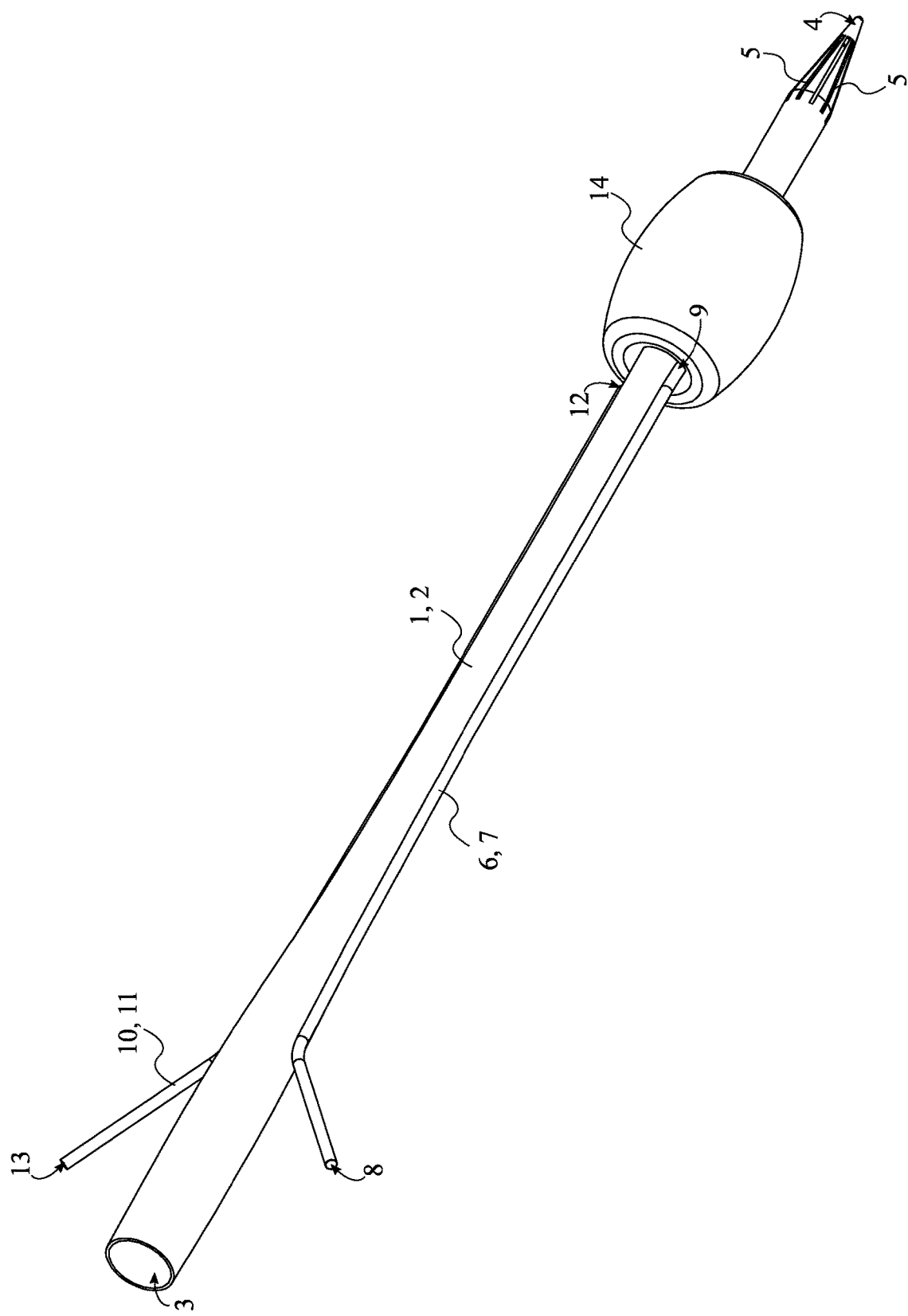
FIG. 4 is a bottom rear perspective view showing the present invention.
Figure 5:
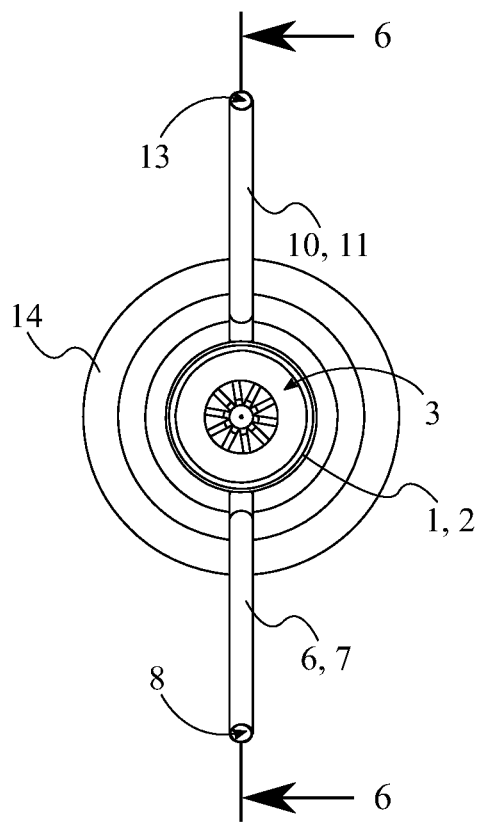
FIG. 5 is a rear view showing the main cannula inlet of the present invention.
Figure 6:
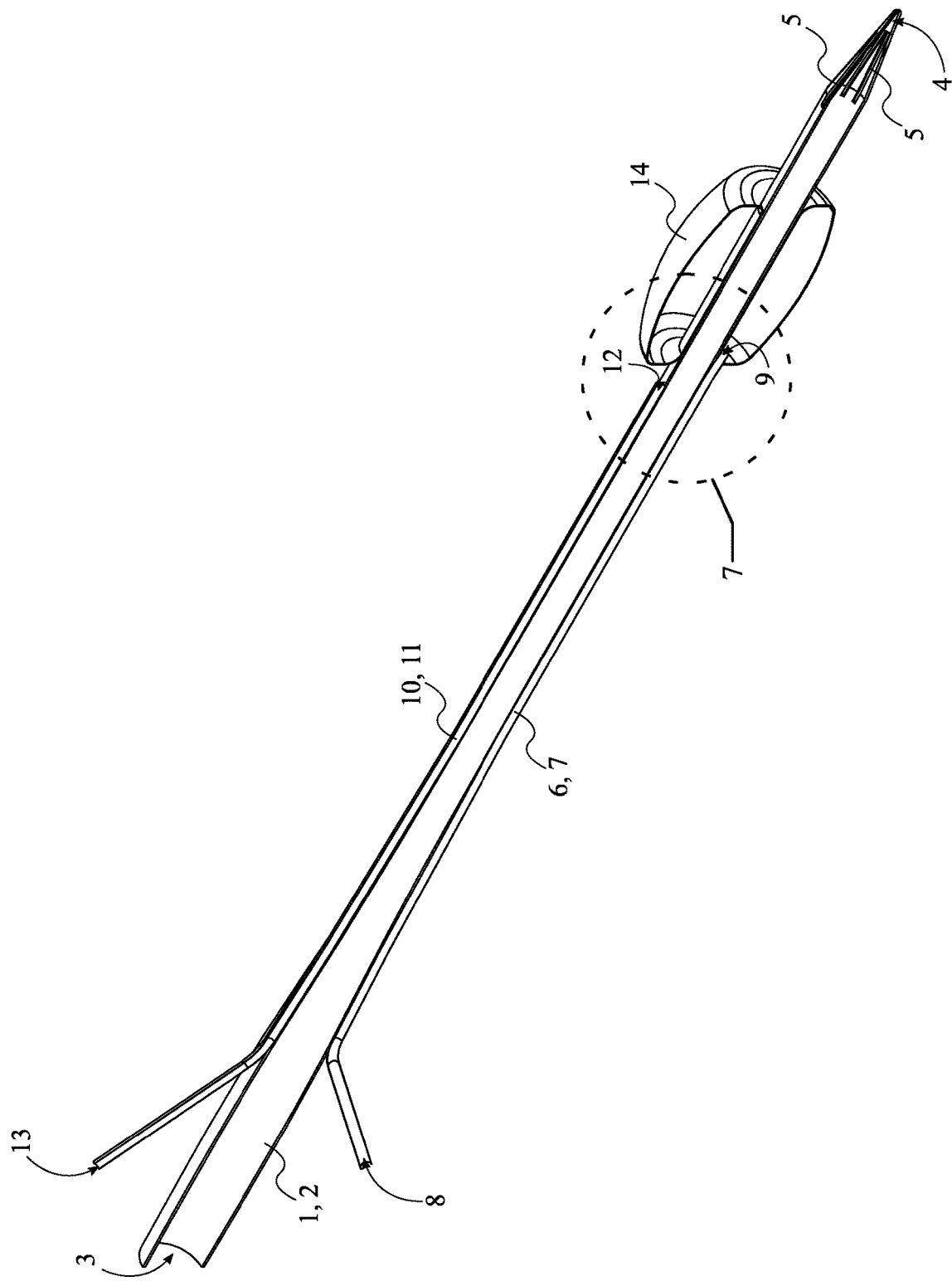
FIG. 6 is a cross-sectional perspective view of the present invention taken in the direction of line 6-6 in FIG. 5.
Figure 7:
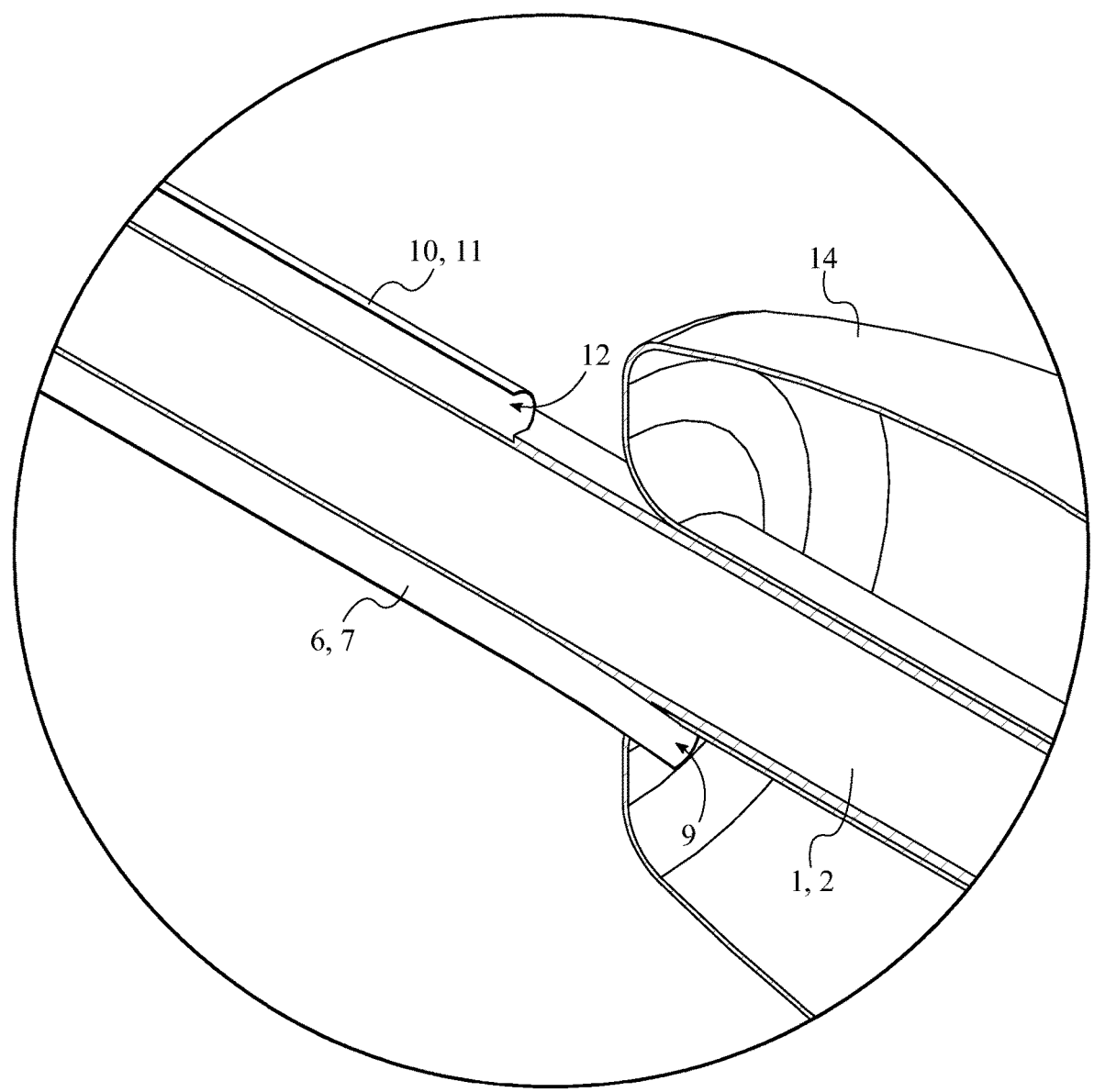
FIG. 7 is a magnified view of the inflation cannula outlet and the drainage cannula inlet shown in FIG. 6.

As can be seen in FIGS. 1 and 2, to facilitate the perfusion of blood into the patient's body, the at least one main cannula 1 may further comprise a plurality of orifices 5 that disperses the blood inflow inside the desired lumen. In addition, the main cannula outlet 4 may be a closed conical end to facilitate the insertion of the present invention into the desired lumen. Further, the plurality of orifices 5 is radially distributed about the main cannula outlet 4 to ensure even dispersal of the blood inflow. The plurality of orifices 5 also traverses through the main cannula outlet 4 to ensure unobstructed dispersal of the blood inflow. The size and shape of the plurality of orifices 5 can be modified according to the size of the main cannula outlet 4 to maintain efficient blood perfusion into the patient's body during the open-heart surgery. Alternatively, the main cannula outlet 4 can be a slanted end with a single large opening.

As can be seen in FIGS. 1 through 4 and 8 through 11, the present invention allows for different connections to be made to the corresponding cannulas during the procedure. To keep the inflation cannula inlet 9 and the drainage cannula outlet 13 separate from each other, the inflation cannula inlet 8 may be positioned offset from the main cannula inlet 3. Similarly, the drainage cannula outlet 13 may be positioned offset from the main cannula inlet 3. This way, the medical staff can connect the appropriate external equipment, such a suction mechanism and an inflation valve 20, to the drainage cannula 10 and the inflation cannula 6.

To facilitate the connection of the present invention to an existing cardiopulmonary bypass circuit (CPB) machine, the present invention may further comprise a Y-connector 15. As can be seen in FIG. 8 through 11, the Y-connector 15 is designed to enable the fluid communication of the CPB machine to the main cannula body 2 as well as to other medical instruments. The Y-connector 15 comprises a connector inlet 16, a first connector outlet 17, and a second connector outlet 18. The connector inlet 16 can be arranged to be in fluid communication with the CPB machine so that the blood inflow is split into two flows that exit through the first connector outlet 17 and the second connector outlet 18. To connect the main cannula body 2 to the Y-connector 15, the first connector outlet 17 is in fluid communication with the main cannula inlet 3. This way, some of the blood inflow from the Y-connector 15 is guided into the main cannula body 2 until the blood exits the main cannula body 2 through the main cannula outlet 4 and into the desired lumen. The second connector outlet 18 can be clamped if unused.

Alternatively, the second connector outlet 18 can be connected to a secondary cannula to perfuse blood into another part of the patient's body. As can be seen in FIG. 8 through 12, to do so, the present invention may further comprise an axillary arterial cannula 19. The axillary arterial cannula 19 enables the perfusion of blood from the same cardiopulmonary bypass circuit into a separate part of the body while still delivering blood into the main desired lumen. So, the axillary arterial cannula 19 is in fluid communication with the second connector outlet 18 to guide the rest of blood inflow from the Y-connector 15 into the secondary lumen for blood perfusion into a separate part of the patient's body. In alternate embodiments, the Y-connector 15 may be utilized to connect the present invention to other medical equipment.

To facilitate the selective inflation of the balloon tamponade 14, the present invention may further comprise an inflation valve 20. As can be seen in FIG. 8 through 11, the inflation valve 20 enables the medical staff to inflate or deflate the balloon tamponade 14 as desired during the procedure. To do so, the inflation valve 20 is in fluid communication with the inflation cannula inlet 8. Thus, the medical staff can inflate the balloon tamponade 14 once the main cannula outlet 4 is placed in the desired position along the target lumen. Once inflated, the balloon tamponade 14 acts as a barrier to prevent blood flow in one direction within the desired lumen as well as to lock the main cannula outlet 4 in place. After the procedure has been performed, the medical staff can deflate the balloon tamponade 14 by disengaging the inflation valve 20 which evacuates the fluid inside the balloon tamponade 14. After the balloon tamponade 14 has been completely deflated, the medical staff can then remove the present invention from the lumen to finish the surgery.

To further facilitate the procedure, the present invention may further comprise a thoracic aortic graft 21. As can be seen in FIG. 8 through 12, the thoracic aortic graft 21 enables the safe performance of the procedure while protecting the organs surrounding the operative area. To do so, the thoracic aortic graft 21 comprises a first open end 22 and a second open end 23. During the procedure, the main cannula body 2 traverses through the thoracic aortic graft 21 so that main cannula outlet 4 can be inserted into the desired lumen. Accordingly, the balloon tamponade 14, the main cannula inlet 3, and the main cannula outlet 4 are positioned external to the thoracic aortic graft 21. Further, the main cannula inlet 3 is positioned adjacent to the first open end 22 while the balloon tamponade 14 and the main cannula outlet 4 are positioned adjacent to the second open end 23. This way, the at least one main cannula 1 along with the inflation cannula 6, the drainage cannula 10, and the balloon tamponade 14 can be inserted and removed as necessary.

Exemplary Method of Use of the Preset Invention

Figure 8:
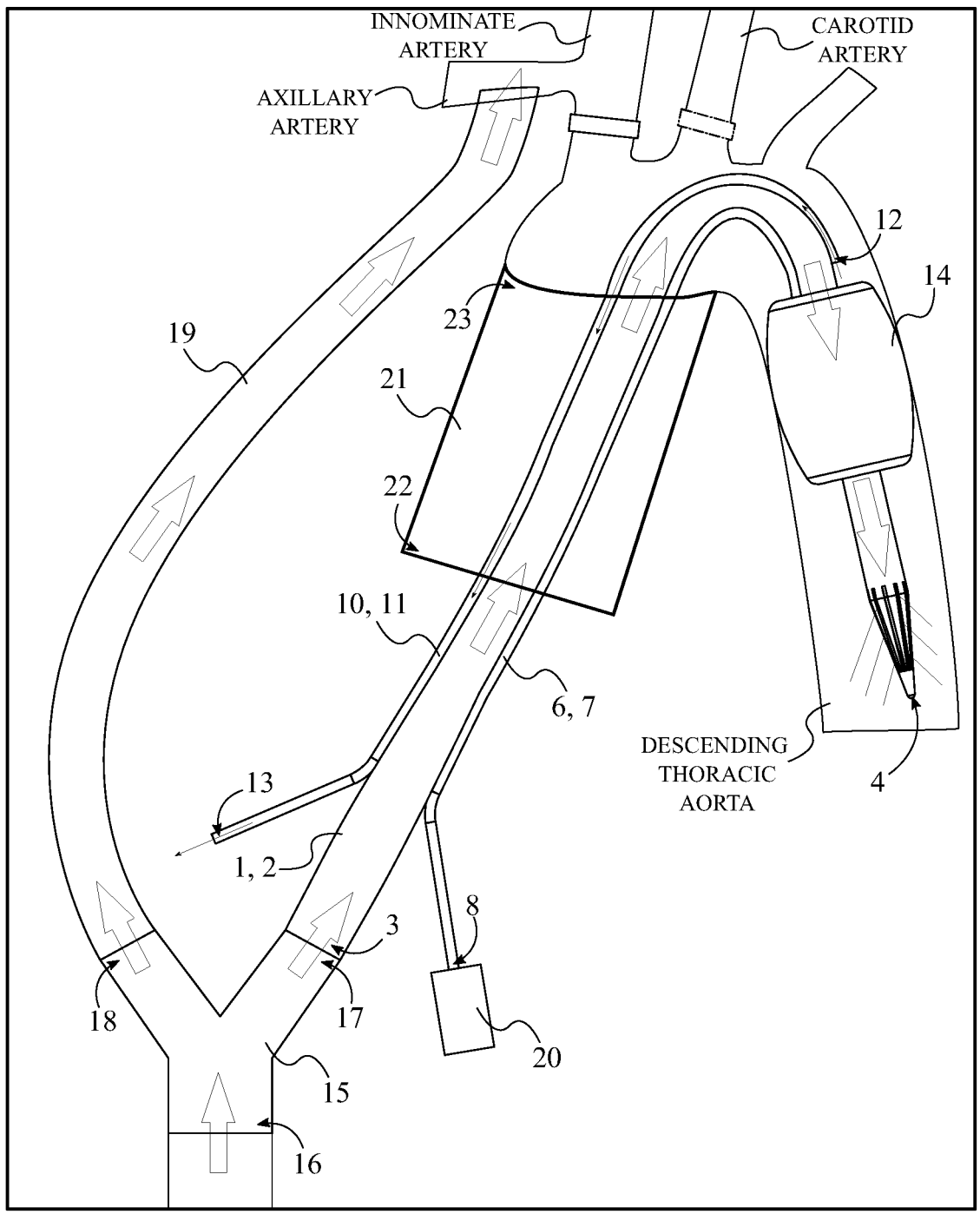
FIG. 8 is a schematic view showing the present invention, wherein the aortic perfusion catheter is shown inserted into the descending thoracic aorta.
Figure 9:
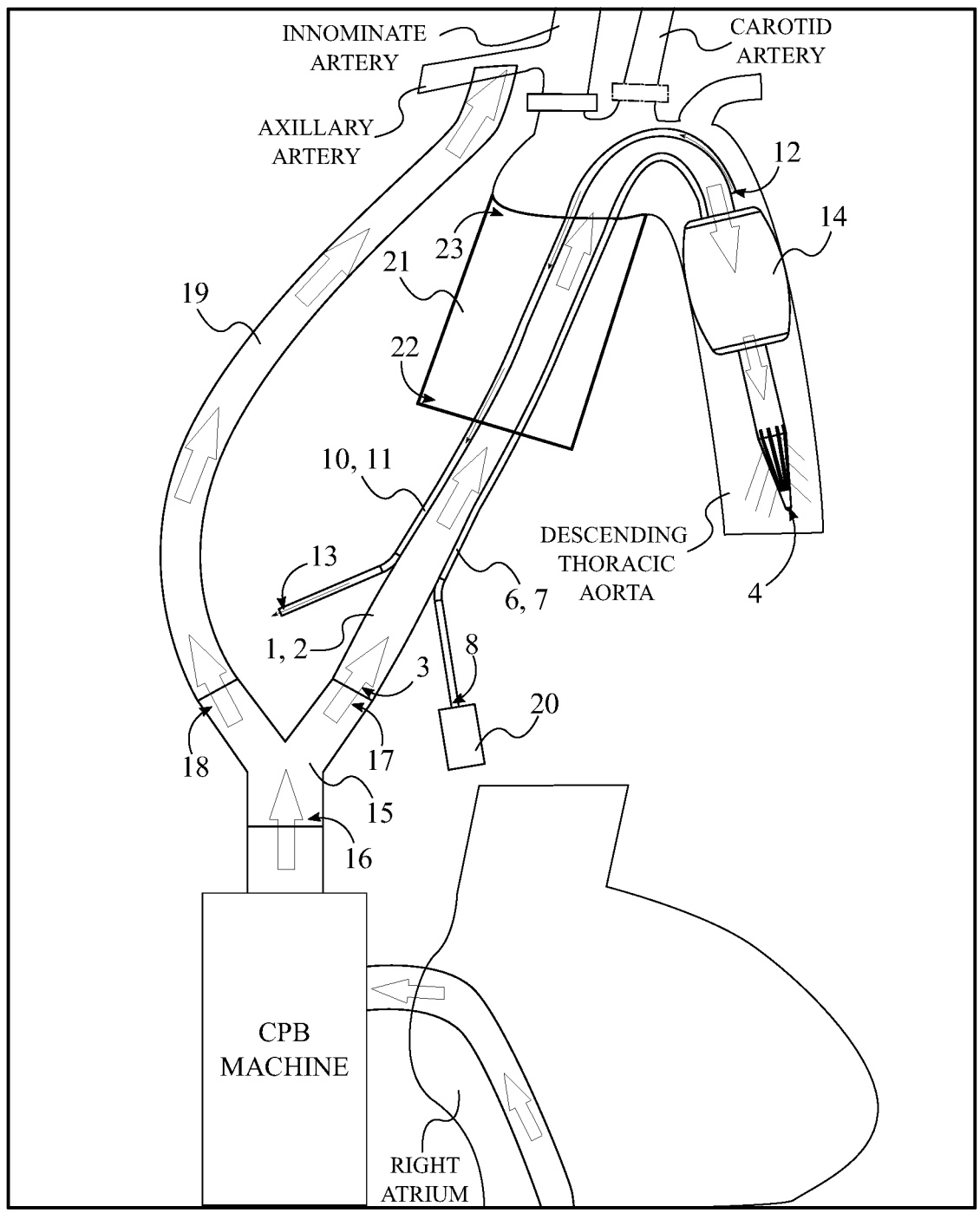
FIG. 9 is a schematic view showing the present invention, wherein the aortic perfusion catheter is shown inserted into the descending thoracic aorta, and wherein the Y-connector is shown connected to a cardiopulmonary bypass (CPB) machine.
Figure 13:
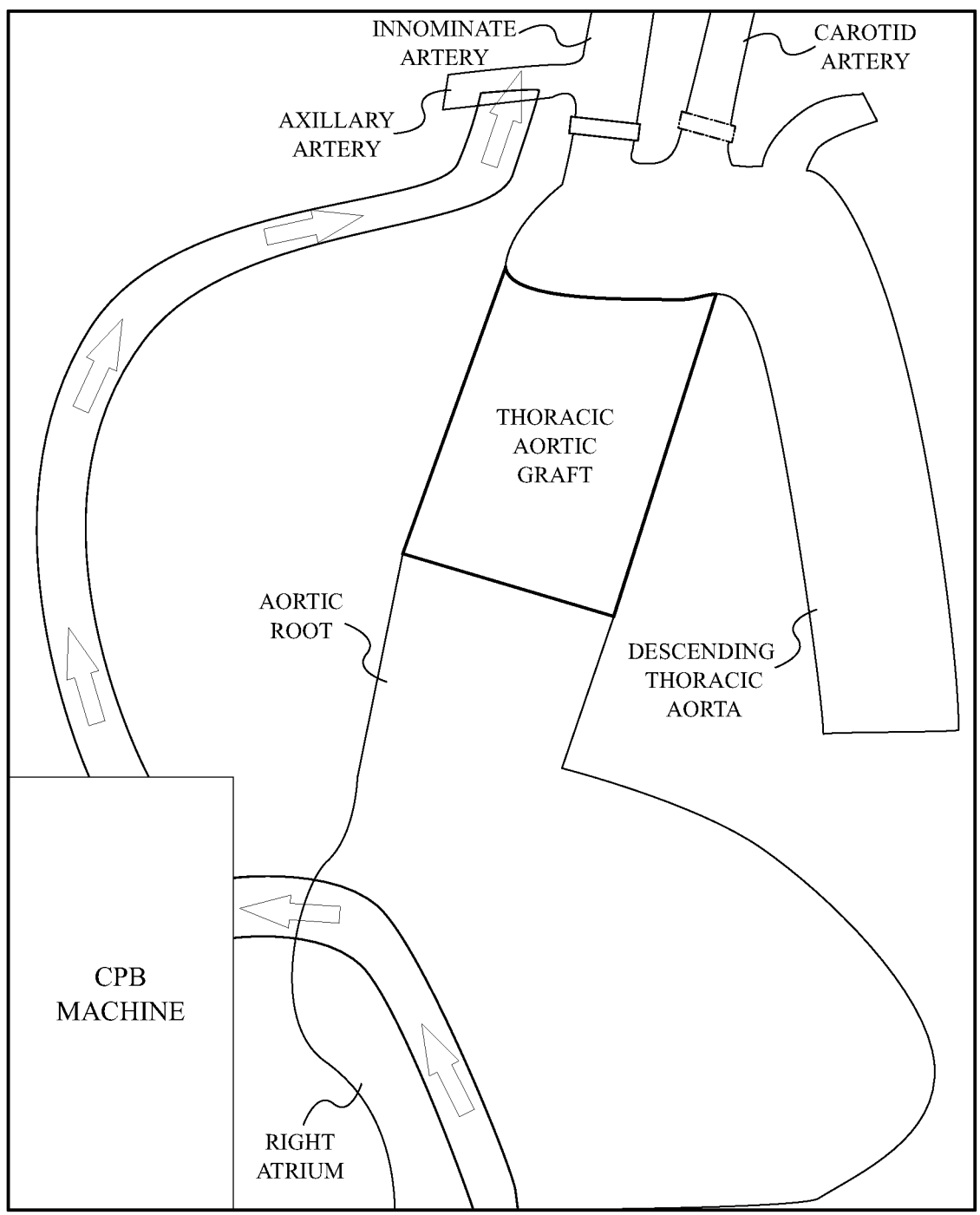
FIG. 13 is a schematic view showing the prior art, wherein a CPB machine is shown used during the repair of acute ascending aortic dissection at −20 degrees C., and wherein antegrade cerebral perfusion through the right axillary artery is performed.

The present invention can be used to maintain perfusion to the rest of the body during repair of the artic arch or the distal ascending aorta. Unlike the traditional procedure shown in FIG. 13, the present invention enables different levels of aortic dissection while mitigating the possible postoperative injuries that occur from the traditional procedure. As can be seen in FIG. 8 through 9, to do so, the thoracic aortic graft 21 is placed on the target aorta for repair. Two vascular clamps are applied to the innominate artery and the carotid artery. The first connector outlet 17 is connected to the main cannula inlet 3, while the connector inlet 16 is connected to the cardiopulmonary bypass circuit. In addition, the inflation valve 20 is connected to the inflation cannula inlet 8, while the drainage cannula outlet 13 is connected to the corresponding suction mechanism. Then, the main cannula body 2 is inserted into the thoracic aortic graft 21 until the main cannula outlet 4 along with the balloon tamponade 14 are positioned within the lumen of the descending thoracic aorta. The balloon tamponade 14 is then inflated to secure the main cannula outlet 4 within the descending thoracic aorta. After everything is secured, the blood flow to the rest of the body is restored while the medical staff performs the surgery.

Figure 10:
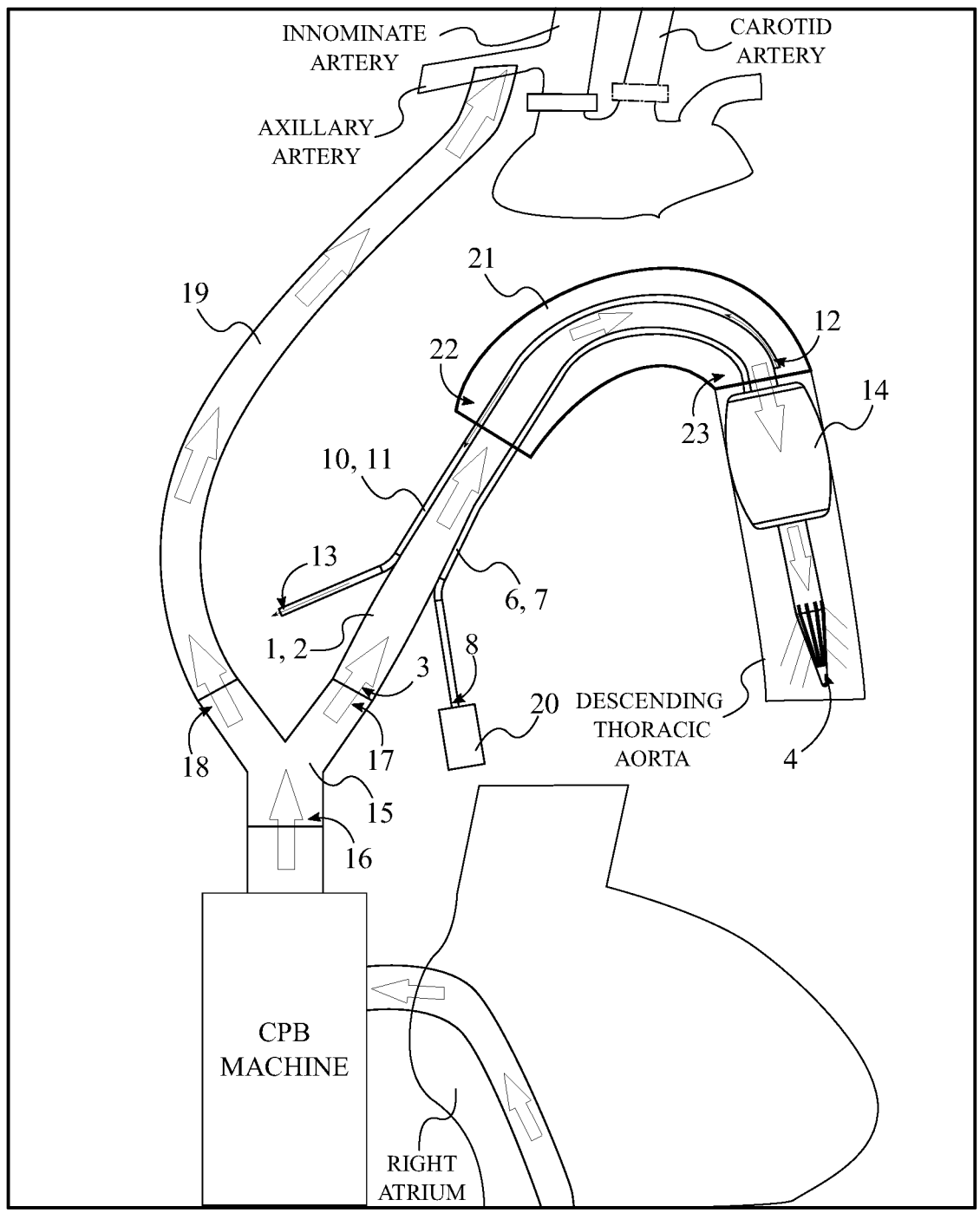
FIG. 10 is a schematic view showing the present invention, wherein the aortic perfusion catheter is shown inserted into the descending thoracic aorta, and wherein the thoracic aortic graft is shown connected to the descending thoracic aorta for more extensive dissection of the aortic arch.
Figure 11:
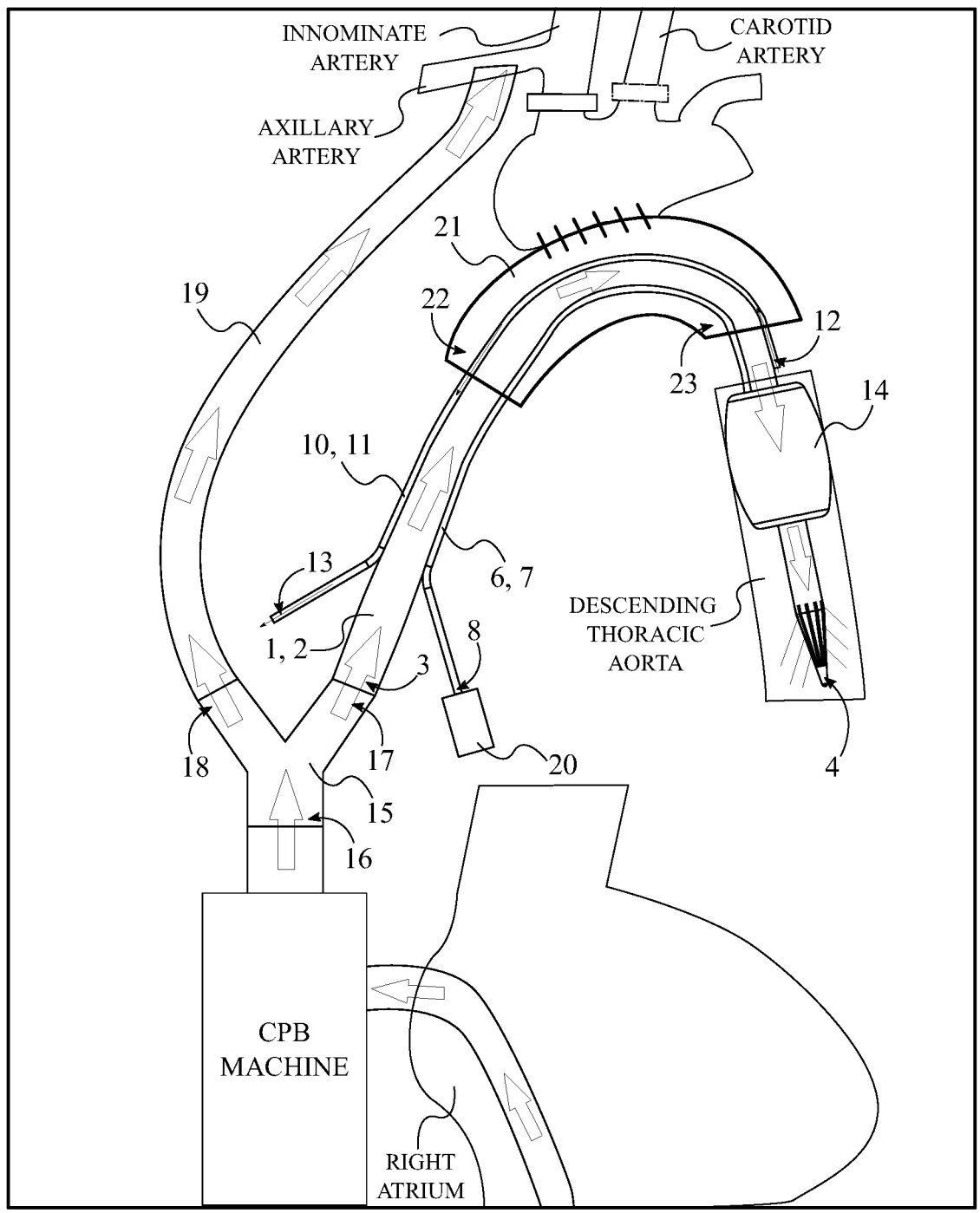
FIG. 11 is a schematic view showing the present invention, wherein the aortic perfusion catheter is shown inserted into the descending thoracic aorta, wherein the thoracic aortic graft is shown connected to the descending thoracic aorta for more extensive dissection of the aortic arch, wherein the distal aortic anastomosis is shown completed, and wherein anastomosis on the island of the aortic arch to snare-ride with thoracic aortic graft.
Figure 12:
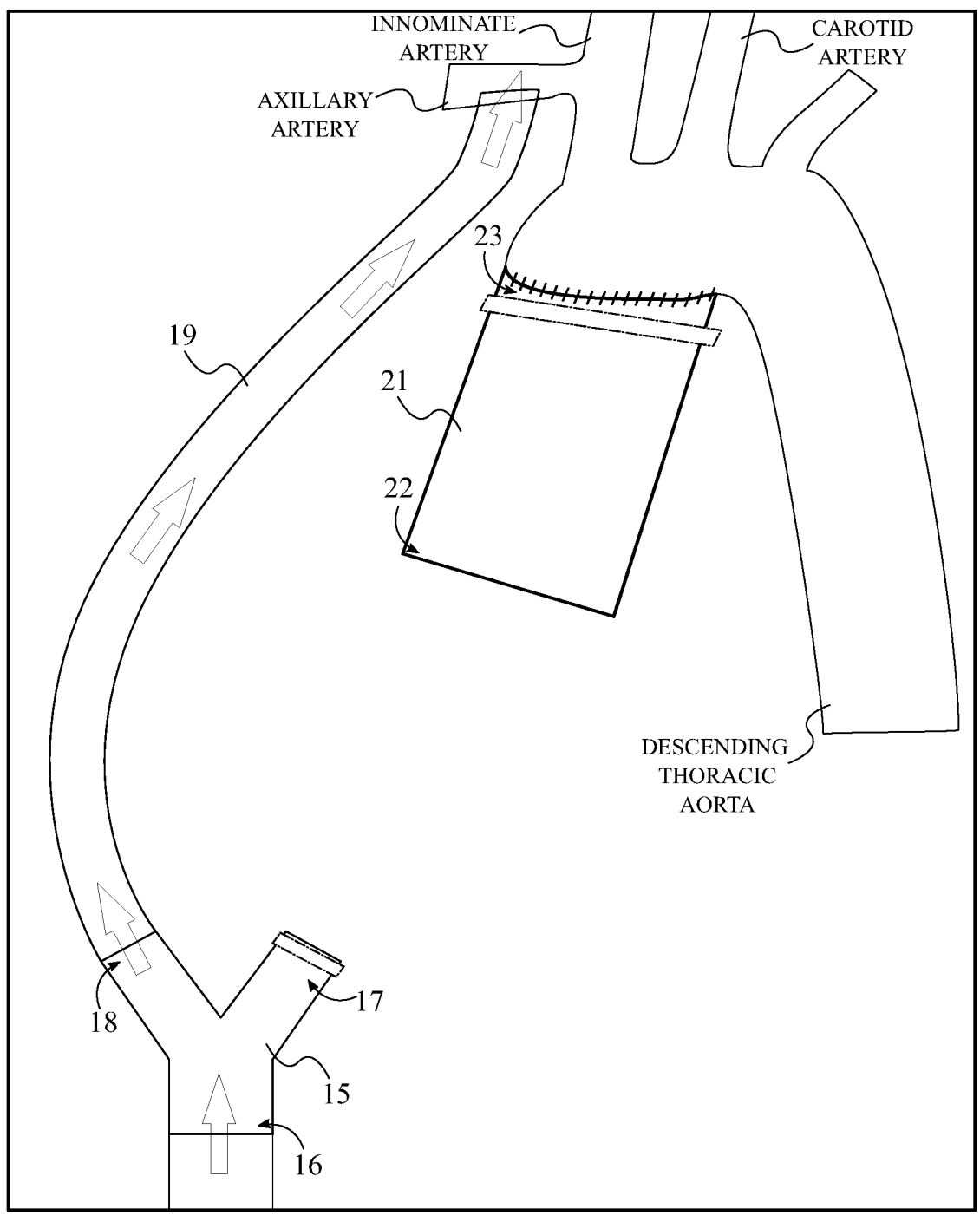
FIG. 12 is a schematic view showing the present invention, wherein the aortic perfusion catheter is shown removed from the descending thoracic aorta, wherein the thoracic aortic graft is shown clamped, and wherein the Y-connector is shown clamped.

Meanwhile, a partial clamp is applied to the axillary arterial cannula 19 that guides the blood flow into the axillary artery and to the brain to about one liter per minute and clamping the origin of the innominate artery. As can be seen in FIG. 8 through 12, the opposite end of the axillary arterial cannula 19 is connected to the second connector outlet 18. During the surgery, the medical staff can remove any fluids present behind the balloon tamponade 14 using the drainage cannula 10. When the distal aortic anastomosis is completed, the balloon tamponade 14 is deflated so that the main cannula body 2 can be removed. An aortic cross-clamp is applied on the thoracic aortic graft 21, and the first connector outlet 17 is also clamped. Then, the vascular clamps on the innominate artery and the carotid artery are removed. Flow to the axillary artery is then restored to normal (about four liters per minute). The patient can then start to be rewarmed with the cardiopulmonary bypass circuit. Finally, the surgeon can start working on the proximal aortic anastomosis or replace the aorta and the aortic valve with composite graft. If more extensive dissection is needed, the thoracic aortic graft 21 can be directly connected to the descending thoracic aorta, as shown in FIGS. 10 and 11.

Although the invention has been explained in relation to its preferred embodiment, it is to be understood that many other possible modifications and variations can be made without departing from the spirit and scope of the invention.

What is claimed is:

1. An aortic perfusion catheter comprising:
   at least one main cannula;
   an inflation cannula;
   a drainage cannula;
   a balloon tamponade;
   the at least one main cannula comprising a main cannula body, a main cannula inlet, and a main cannula outlet;
   the inflation cannula comprising an inflation cannula body, an inflation cannula inlet, and an inflation cannula outlet;
   the drainage cannula comprising a drainage cannula body, a drainage cannula inlet, and a drainage cannula outlet;
   the inflation cannula body and the drainage cannula body being laterally connected to the main cannula body;
   the inflation cannula body and the drainage cannula body being positioned offset to each other;
   the balloon tamponade being laterally connected around the main cannula body, adjacent to the main cannula outlet;
   the inflation cannula inlet being positioned adjacent to the main cannula inlet;
   the inflation cannula outlet hermetically traversing into the balloon tamponade;
   the drainage cannula inlet being positioned external to the balloon tamponade;
   and,
   the drainage cannula outlet being positioned adjacent to the main cannula inlet;
   a Y-connector;
   the Y-connector comprising a connector inlet, a first connector outlet, and a second connector outlet;
   the first connector outlet being in fluid communication with the main cannula inlet;
   an auxiliary arterial cannula; and,
   the auxiliary arterial cannula being in fluid communication with the second connector outlet;
   a thoracic aortic graft;
   the thoracic aortic graft comprising a first open end and a second open end;

the main cannula body traversing through the thoracic aortic graft;

the balloon tamponade, the main cannula inlet, and the main cannula outlet being positioned external to the thoracic aortic graft;

the main cannula inlet being positioned adjacent to the first open end; and, the balloon tamponade and the main cannula outlet being positioned adjacent to the second open end.

2. The aortic perfusion catheter as claimed in claim 1 comprising:
the at least one main cannula further comprising a plurality of orifices located at the outlet, which has a closed conical end;
the main cannula outlet being a closed conical end;
the plurality of orifices being radially distributed about the main cannula outlet; and,
the plurality of orifices traversing through the main cannula outlet.

3. The aortic perfusion catheter as claimed in claim 1, wherein the inflation cannula inlet is positioned offset from the main cannula inlet.

4. The aortic perfusion catheter as claimed in claim 1, wherein the drainage cannula outlet is positioned offset from the main cannula inlet.

5. The aortic perfusion catheter as claimed in claim 1 comprising:
an inflation valve; and,
the inflation valve being in fluid communication with the inflation cannula inlet.

6. An aortic perfusion catheter comprising:
at least one main cannula;
an inflation cannula;
a drainage cannula;
a balloon tamponade;
the at least one main cannula comprising a main cannula body, a main cannula inlet, a main cannula outlet, and a plurality of orifices;
the inflation cannula comprising an inflation cannula body, an inflation cannula inlet, and an inflation cannula outlet;
the drainage cannula comprising a drainage cannula body, a drainage cannula inlet, and a drainage cannula outlet;
the main cannula outlet being a closed conical end;
the inflation cannula body and the drainage cannula body being laterally connected to the main cannula body;
the inflation cannula body and the drainage cannula body being positioned offset to each other;
the balloon tamponade being laterally connected around the main cannula body, adjacent to the main cannula outlet;
the inflation cannula inlet being positioned adjacent to the main cannula inlet;
the inflation cannula outlet hermetically traversing into the balloon tamponade;
the drainage cannula inlet being positioned external to the balloon tamponade;
the drainage cannula outlet being positioned adjacent to the main cannula inlet;
the plurality of orifices being radially distributed about the main cannula outlet; and,
the plurality of orifices traversing through the main cannula
a Y-connector;
an axillary arterial cannula;
the Y-connector comprising a connector inlet, a first connector outlet, and a second connector outlet;
the first connector outlet being in fluid communication with the main cannula inlet; and,
the auxiliary arterial cannula being in fluid communication with the second connector outlet;
a thoracic aortic graft;
the thoracic aortic graft comprising a first open end and a second open end;
the main cannula body traversing through the thoracic aortic graft;
the balloon tamponade, the main cannula inlet, and the main cannula outlet being positioned external to the thoracic aortic graft;
the main cannula inlet being positioned adjacent to the first open end; and,
the balloon tamponade and the main cannula outlet being positioned adjacent to the second open end.

7. The aortic perfusion catheter as claimed in claim 6, wherein the inflation cannula inlet is positioned offset from the main cannula inlet.

8. The aortic perfusion catheter as claimed in claim 6, wherein the drainage cannula outlet is positioned offset from the main cannula inlet.

9. The aortic perfusion catheter as claimed in claim 6 comprising:
an inflation valve; and,
the inflation valve being in fluid communication with the inflation cannula inlet.

10. An aortic perfusion catheter comprising:
at least one main cannula;
an inflation cannula;
a drainage cannula;
a balloon tamponade;
the at least one main cannula comprising a main cannula body, a main cannula inlet, a main cannula outlet, and a plurality of orifices;
the inflation cannula comprising an inflation cannula body, an inflation cannula inlet, and an inflation cannula outlet;
the drainage cannula comprising a drainage cannula body, a drainage cannula inlet, and a drainage cannula outlet;
the main cannula outlet being a closed conical end;
the inflation cannula body and the drainage cannula body being laterally connected to the main cannula body;
the inflation cannula body and the drainage cannula body being positioned offset to each other;
the balloon tamponade being laterally connected around the main cannula body, adjacent to the main cannula outlet;
the inflation cannula inlet being positioned adjacent to the main cannula inlet;
the inflation cannula inlet being positioned offset from the main cannula inlet;
the inflation cannula outlet hermetically traversing into the balloon tamponade;
the drainage cannula inlet being positioned external to the balloon tamponade;
the drainage cannula outlet being positioned adjacent to the main cannula inlet;
the drainage cannula outlet being positioned offset from the main cannula inlet;
the plurality of orifices being radially distributed about the main cannula outlet; and,
the plurality of orifices traversing through the main cannula outlet;
a Y-connector;
an axillary arterial cannula;

the Y-connector comprising a connector inlet, a first connector outlet, and a second connector outlet;

the first connector outlet being in fluid communication with the main cannula inlet; and, the auxiliary arterial cannula being in fluid communication with the second connector outlet;

a thoracic aortic graft;

the thoracic aortic graft comprising a first open end and a second open end;

the main cannula body traversing through the thoracic aortic graft;

the balloon tamponade, the main cannula inlet, and the main cannula outlet being positioned external to the thoracic aortic graft;

the main cannula inlet being positioned adjacent to the first open end; and, the balloon tamponade and the main cannula outlet being positioned adjacent to the second open end.

11. The aortic perfusion catheter as claimed in claim 10 comprising:

an inflation valve; and, the inflation valve being in fluid communication with the inflation cannula inlet.

* * * * *